United States Patent
Yam

[11] Patent Number: 6,015,547
[45] Date of Patent: Jan. 18, 2000

[54] STABLE SOLUTION OF ZINC IONS AND BICARBONATE AND/OR CARBONATE IONS

[75] Inventor: Benny S. Yam, Holmdel, N.J.

[73] Assignee: Church & Dwight Co., Inc., Princeton, N.J.

[21] Appl. No.: 09/222,101

[22] Filed: Dec. 29, 1998

Related U.S. Application Data

[63] Continuation-in-part of application No. 08/957,904, Oct. 27, 1997, Pat. No. 5,855,873.

[51] Int. Cl.$^7$ .............................. A61K 7/16; A61K 7/36; A61K 31/315; A61K 33/30

[52] U.S. Cl. .......................... 424/49; 424/462; 424/717; 424/67

[58] Field of Search ............................... 424/49–58, 642, 424/717

[56] References Cited

U.S. PATENT DOCUMENTS

| | | | |
|---|---|---|---|
| 3,887,704 | 6/1975 | Lichtenstein | 424/145 |
| 4,132,770 | 1/1979 | Barth . | |
| 4,289,755 | 9/1981 | Dhabar | 424/52 |
| 4,292,324 | 9/1981 | Jönsson et al. | 424/145 |
| 4,312,889 | 1/1982 | Melsheimer . | |
| 4,568,540 | 2/1986 | Asano et al. | 424/52 |
| 4,666,708 | 5/1987 | Goldemberg et al. . | |
| 4,992,259 | 2/1991 | Sohiraldi et al. | 424/49 |
| 5,076,960 | 12/1991 | Hutchings et al. | 252/186.33 |
| 5,182,099 | 1/1993 | Jonsson et al. | 424/49 |
| 5,185,153 | 2/1993 | Pollock . | |
| 5,302,373 | 4/1994 | Gracin et al. | 424/49 |
| 5,330,749 | 7/1994 | Giacin et al. . | |
| 5,455,023 | 10/1995 | Giacin et al. . | |
| 5,456,902 | 10/1995 | Williams et al. . | |
| 5,541,165 | 7/1996 | Turgeon . | |
| 5,554,358 | 9/1996 | Williams et al. . | |
| 5,587,147 | 12/1996 | Domke et al. | 424/49 |
| 5,593,670 | 1/1997 | Trinh et al. . | |
| 5,616,313 | 4/1997 | Williams et al. | 424/49 |
| 5,632,972 | 5/1997 | Williams et al. | 424/49 |
| 5,753,217 | 5/1998 | Christopfel | 424/53 |
| 5,855,873 | 1/1999 | Yam . | |

OTHER PUBLICATIONS

The Merck Index, 12th Ed. (1996), pp. 1374, 1680, & 1733–1736; Re Entries: #8178; #9983; #10259; #10260; #10269; #10272; #10273; #10279; #10281; #10282; #10283; #10286; #10288; #10292; #10293; & #10295.

*Primary Examiner*—Shep K. Rose
*Attorney, Agent, or Firm*—Irving Fishman

[57] ABSTRACT

A storage stable aqueous solution or aqueous gel of zinc ions in the presence of bicarbonate ions is disclosed. The solution comprises: (a) a source of zinc ion, (b) a source of a stabilizing anion which can stabilize soluble zinc and bicarbonate and/or carbonate in solution; (c) a source of bicarbonate ion; and (d) a solvent therefor. The solvent comprises a major proportion of water. The zinc salt is present in an amount suitable for the intended purpose; the stabilizing anion in an amount B of at least 1.2 equivalents per equivalent of zinc ion; and the bicarbonate ion cannot exceed certain levels which are related to the level of the stabilizing anion.

20 Claims, No Drawings

STABLE SOLUTION OF ZINC IONS AND BICARBONATE AND/OR CARBONATE IONS

CROSS-REFERENCE TO RELATED APPLICATIONS

This application is a continuation-in-part of U.S. application Ser. No. 08/957,904, filed Oct. 27, 1997, now U.S. Pat. No. 5,855,873.

STATEMENT REGARDING FEDERALLY SPONSORED RESEARCH OR DEVELOPMENT

Not Applicable

FIELD OF THE INVENTION

The present invention relates generally to aqueous formulations, particularly aqueous solutions, pastes, creams, lotions, and gels having zinc ion in the presence of bicarbonate and/or carbonate ions, all in solution in a single phase. The invention relates in particular to use of such pastes, creams, lotions, gels, and solutions (including sprays), in formulations for mouthwashes; breath fresheners; ostomy and incontinence deodorants; foot deodorants; underarm deodorants and antiperspirants; hand soap; hair care products (such as shampoos and conditioners); laundry detergents; animal litter deodorants; fabric/carpet/upholstery deodorizers; household and industrial hard surface cleaners; toilet deodorizers/sanitizers; agricultural fungicides; dental pastes, gels and polishing liquids; air fresheners; etc. In short, the present invention relates to the use of zinc ion in the presence of bicarbonate and/or carbonate ion where both are required (or desired) to be simultaneously in solution in a single phase.

BACKGROUND OF THE INVENTION

Zinc ion has been used in oral products for some time now. In dentifrices, it has been employed as a tartar control agent. In mouthwashes as well as elsewhere, it is used as a bacteriocide (U.S. Pat. No. 5,455,023, incorporated herein by reference) and to combat malodor. In other products it has been used as a bacteriocide or as a fungicide. Zinc undecylenate, for example is a water insoluble antifungal. Zinc tannate, zinc carbonate, and zinc peroxide are antiseptic/astringents which are practically insoluble in water. Zinc phenolsulfonate is an astringent. Zinc sulfate has been used as an ophthalmic astringent and as a zinc supplement. Zinc salicylate, zinc permanganate, and zinc stearate are antiseptic/astringents. Zinc pyrithione is a fungicide, bacteriocide, and antiseborrheic; it is the active agent in Head & Shoulders brand shampoo. Zinc propionate is a topical antifungal. Zinc oxide is an astringent/protectorant. Zinc nitrate is used in dying textiles. Zinc metaarsenate is a wood preservative and insecticide. Zinc iodide is an antiseptic/astringent. Zinc iodate is an antiseptic. Zinc chloride is an astringent. All of these can be found in The Merck Index, 12th Edition, Merck & Co. (Whitehouse Station, N.J. 1996). Zinc borate, zinc caprylate, and zinc ricinolate are fungicides. Bicarbonate compounds have been used in oral care products for a variety of purposes including, but not limited to, buffering capacity, as alkalinizing agents, as abrasives (as solid particles), for deodorizing activity, and providing for a clean "mouthfeel" and a refreshing aftertaste in the oral cavity. Exemplary patents dealing with mouthwashes or rinses having bicarbonate included include, but are not limited to U.S. Pat. No. 4,132,770; U.S. Pat. No. 4,312,889; U.S. Pat. No. 4,666,708; U.S. Pat. No. 5,185,153; U.S. Pat. No. 5,302,373; U.S. Pat. No. 5,330,749, U.S. Pat. No. 5,455,023; U.S. Pat. No. 5,541,165; and U.S. Pat. No. 5,587,147; all of which are incorporated herein by reference. Carbonates or mixtures of carbonates and bicarbonates have been used similarly where the desired pH is not high enough when using bicarbonate compounds alone. Carbonates, especially alkali metal carbonates, have also been used extensively in the detergent (especially laundry and dishwashing) and household and industrial cleaner fields primarily as alkalinity providers or builders.

It has therefore been deemed advantageous to try to combine, in a single phase of a formulation, both zinc ion containing compounds and bicarbonate and/or carbonate ion containing compounds, each of which is in solution. Unfortunately this has not been possible previously. Zinc ion typically reacts with bicarbonate ion to result in liberation of carbon dioxide and the formation of various insoluble basic salts of zinc and carbonate. Attempts to get around this technical difficulty have included keeping the two components separated in different compartments or containers until ready for use; encapsulating one or both of the ingredients; or presenting one or both of the components in less soluble form so that the two species are in limited contact until diluted by the user in the course of using the product, among others.

Examples of encapsulating one or both components include U.S. Pat. No. 5,302,373; U.S. Pat. No. 5,330,749; and U.S. Pat. No. 5,455,023. Examples of dual compartment dispensing include U.S. Pat. No. 5,456,902; U.S. Pat. No. 5,554,358; U.S. Pat. No. 5,616,313; and U.S. Pat. No. 5,632,972. Examples of complexation include U.S. Pat. No. 5,587,147. All of the foregoing U.S. patents are incorporated herein by reference. Typical of the presentation of one or more of the components in an insoluble or slightly soluble form until use is in the toothpaste, tooth gel and tooth powder areas where their remaining in solution during storage may not be as critical a requirement to meet. (Notwithstanding this lack of criticality for keeping the zinc ion and the bicarbonate and/or carbonate ion in solution, it is still highly desirable to maintain both components in solution above the concentrations that would be achieved without the solubilizing anion of the invention.)

However, many liquid products (such as mouthwashes and many other applications mentioned above) cannot present with precipitates during storage and still be considered suitable delivery vehicles for the components they contain. Haircare products are typically in contact with the scalp for such a short period of time that dissolution of particulate zinc compounds, especially zinc carbonates (inclusive of bicarbonates and sesquicarbonates), to obtain the benefit of zinc ion is truly not a suitable result. Furthermore, many of the applications above require clarity for improved consumer acceptance or aesthetics. Additionally, dual dispensing systems are inconvenient for the user and generally not desirable. As such, there has been a long felt need for a single phase stable solution having both zinc ion and bicarbonate and/or carbonate ion, each in solution.

OBJECTS OF THE INVENTION

It is therefore an object of the invention to provide a single phase, stable aqueous solution, paste, cream, lotion, and/or gel having both zinc ion and bicarbonate and/or carbonate ion, each in solution.

It is another object of the invention to provide a single phase stable solution having both zinc ion and bicarbonate and/or carbonate ion, each in solution, in amounts which are effective for the prevention and/or counteracting of malodors.

It is another object of the invention to provide a single phase stable aqueous solution (inclusive of lotions), aqueous cream, aqueous paste, or aqueous gel having both zinc ion and bicarbonate and/or carbonate ion, each in solution, in amounts which are effective to elicit both the antibacterial and/or the astringent action of zinc ion and the deodorant and/or alkalinizing capability of bicarbonate and/or carbonate ion.

Another object of the invention is to provide an oral care solution, paste, cream, lotion, or gel (such as a mouthwash, a toothpaste, a toothgel, or a breath freshener) having both zinc ion and bicarbonate and/or carbonate ion, each in solution.

A further object of the invention is to provide an external body care deodorant product (such as an ostomy deodorant, an incontinence deodorant, a foot deodorant, an underarm deodorant, a hand soap, or a shampoo and/or conditioner) having both zinc ion and bicarbonate and/or carbonate ion, each in solution.

Still a further object of the invention is to provide a home care product (such as a laundry detergent, a pet litter deodorant, or a household deodorizing cleaner) having both zinc ion and bicarbonate and/or carbonate ion, each in solution.

Yet another object of the invention is to provide an industrial deodorizing cleaner having both zinc ion and bicarbonate and/or carbonate ion, each in solution.

An even further object of the invention is to provide powder or effervescent tablet for dissolution by the user, the solution to contain stably dissolved in a single phase each of zinc ion and bicarbonate and/or carbonate ion.

Still other objects of the invention will be appreciated by those of ordinary skill in the art.

BRIEF SUMMARY OF THE INVENTION

These and other objects of the invention can be achieved by a storage stable aqueous solution, paste, cream, lotion, or gel of zinc ions in the presence of bicarbonate and/or carbonate ions where the aqueous phase comprises:

(a) a zinc ion source;

(b) a source of a stabilizing anion which stabilizes solutions of zinc ions in the presence of bicarbonate and/or carbonate ions;

(c) a bicarbonate and/or carbonate ion source; and (d) a solvent therefor, said solvent comprising a major proportion of water; and said stabilizing anion being selected from anions of organic di-, tri-, and poly-acids and di-, tri-, and poly- phosphates;

said zinc ions being present in an amount A of from about 0.01 to about 2 weight said stabilizing anion present in an amount B, which is at least 1.2 equivalents per equivalent of zinc ion;

said bicarbonate and/or carbonate being present in an amount of C equivalents, which is no greater than the sum of (a) (6)×(the number of equivalents of said anions of di-, tri-, or poly-phosphates); and (b) $\{(3^{(n-1)})/(2^m)\}$×(the number of equivalents of said anions of organic di-, tri-, or poly- acids), where n is the number of carboxyl groups and m is the number of basic nitrogens.

Additional amounts of bicarbonate/carbonate, zinc source compound, and/or stabilizing anion source compound may be present in the non-aqueous phase, if desired. Sufficient non-aqueous phase stabilizing anion compound need only be present to the extent that during storage, additional amounts of either the zinc compound or the bicarbonate/carbonate compound(s) will migrate into the aqueous phase and become dissolved.

BRIEF DESCRIPTION OF THE SEVERAL VIEWS OF THE DRAWING

Not Applicable

DETAILED DESCRIPTION OF THE INVENTION

The present invention is directed to a single phase storage stable aqueous solution, lotion, cream, paste, or gel of a zinc salt and a bicarbonate and/or carbonate salt (exclusive of zinc carbonate salts). It is well known that zinc ion and bicarbonate and/or carbonate ion will interact in solution to ultimately form insoluble salts of zinc carbonate(s). These may be zinc carbonate, zinc sesquicarbonate or other combinations of zinc and carbonate ions. Since it is desirable to have both zinc ion and bicarbonate and/or carbonate ion present in the same solution for a variety of purposes, creating a storage stable solution of these species has been long sought after. The present invention accomplishes this desired result.

The invention results in a storage stable single phase solution of these ions by combining a zinc ion source, a source of a stabilizing anion, and a bicarbonate and/or carbonate source, in an aqueous vehicle. While it is advantageous that the vehicle be predominately water, the final formulation may contain solid materials so long as there is an aqueous phase in which the zinc ions and bicarbonate and/or carbonate ions remain in solution together.

For example, a typical aqueous solution of the invention may then be incorporated into a cream, lotion, paste, or gel. In addition, the aqueous solution of the invention may also be incorporated into an emulsion where the aqueous phase is either the external or internal phase. Also, the solution of the present invention may be loaded onto and/or absorbed by other materials, such as clay animal liters, or impregnated into absorbent materials such as incontinence pads and diapers. In such cases, the product may appear dry externally, but may still have microenvironments having zinc ions and bicarbonate and/or carbonate ions in solution in a single phase within the porous matrix of the material. Where such micro-environments exist, the product per se is within the scope of the present invention. Where such aqueous micro-environments do not exist, the manufacture of the product is within the invention as well as the use of the product once it is wet with an aqueous liquid as the dry powder having the zinc ion source, bicarbonate and/or carbonate source, and stabilizing anion source in the correct proportions readily dissolves in the presence of an aqueous environment to result in a solution within the scope of the present invention.

So long as both the bicarbonate and/or carbonate ion and the zinc ion remain in solution in the same phase within the limits of the invention, a formulation with a relatively low total water content is still within the scope of the present invention. The remainder of the formulation can vary over wide ranges so long as the other components in the aqueous phase (or intended to be in the aqueous phase upon contact with water) are compatible with both zinc ion and bicarbonate and/or carbonate ion. Components which are not in (and not intended to be in) the aqueous phase of the product can also vary over wide ranges as long as they either (1) do not migrate into the aqueous phase prior to use, (2) do not adversely affect the stabilized bicarbonate and/or carbonate ion-zinc ion in the aqueous phase if they do migrate into the aqueous phase, and (3) do not adversely affect the end use effectiveness of the bicarbonate and/or carbonate ion and zinc ion.

Optional components of the vehicle vary with the end use of the product so long as they are compatible with the zinc source; the bicarbonate and/or carbonate source; and the stabilizing anion source.

The solutions set forth above may be incorporated into suitable carrier formulations typical of the field of use for the particular product, provided that such carrier does not adversely affect the stabilized solution of zinc ions, bicarbonate/carbonate ions, and stabilizing anions. Any of the optional ingredients mentioned above may also be present in the particular carrier. Further details concerning the optional carrier ingredients is set forth more fully below.

More specifically, the invention is a storage stable aqueous solution, cream, paste, lotion, or gel of zinc ions in the presence of bicarbonate and/or carbonate ions which results from providing, in a single solution:

(a) a zinc ion source;
(b) a source of a stabilizing anion which stabilizes solutions of zinc ions in the presence of bicarbonate and/or carbonate ions;
(c) a bicarbonate and/or carbonate ion source; and
(d) a solvent therefor, said solvent comprising a major proportion of water;

said stabilizing anion being selected from anions of organic di-, tri, and poly-acids and di-, tri, and poly-phosphates;

said zinc ions being present in an amount A of from about 0.01 to about 2 weight preferably about 0.02 to about 1 weight %, more preferably about 0.04 to about 0.5 weight %, even more preferably about 0.08 to about 0.25 weight %, most preferably about 0.12 weight %;

said stabilizing anion present in an amount B, which is at least 1.2 equivalents per equivalent of zinc ion;

said bicarbonate being present in an amount of C equivalents, which is no greater than the sum of
(a) (6)×(the number of equivalents of said anions of di-, tri-, or poly-phosphates); and
(b) $\{(3^{(n-1)})/(2^m)\}$×(the number of equivalents of said anions of organic di-, tri-, or poly- acids), where n is the number of carboxyl groups and m is the number of basic nitrogens.

Additional amounts of bicarbonate/carbonate, zinc source copmpound, and/or stabilizing anion source compound may be present in the non-aqueous phase, if desired. Sufficient non-aqueous phase stabilizing anion compound need only be present to the extent that both (1) during storage, additional amounts of either the zinc compound or the bicarbonate/carbonate compound(s) migrate into the aqueous phase and become dissolved and (2) a clear solution for presentation to the consumer is desired. Where clarity of the product is not at issue, the product can have any additional amounts of carbonate/bicarbonate and/or zinc ion source. As long as upon filtration to remove any precipitate and other none aqueous components, the aqueous solution has both zinc ion and bicarbonate/carbonate ion in solution within the limtis set forth herein for the solution, the product is within the present invention.

The zinc source can be any zinc containing compound which is acceptable to the ultimate utility to which the solution is intended. Hence, in the mouthwash field, the zinc source, as well as the other components must be selected from orally acceptable zinc acompounds. This restriction is not required when the solution is being prepared for conversion of the compounds in other reactions and are not intended to be used in or on the body. For non-oral, topically used formulations the zinc ion source can be any topically acceptable zinc compound which is acceptable to the end purpose of the formulation. Those of ordinary skill in these fields will appreciate such distinctions in applying the invention to applications beyond those of oral and topical personal care products. For example, where zinc ion containing compounds are utilized in applications, such as in deodorants or shampoos, and it is desirable to have bicarbonate and/or carbonate ion also present, and maintain the zinc and bicarbonate and/or carbonate ions in solution, the components need only be acceptable for deodorant or shampoo application and need not be limited to orally acceptable compounds.

It is also well within the invention to provide deodorizing capability to zinc compound formulations in virtually any context in which zinc compounds are employed. Hence, those of ordinary skill will be readily able to modify existing formulations having zinc ions to those of the invention. Similarly, it is within the present invention to provide zinc ion's antibacterial properties to virtually any bicarbonate and/or carbonate ion containing formulation where such properties may be desired, and those of ordinary skill will now be readily able to convert known bicarbonate and/or carbonate ion containing formulations to those of the present invention.

The Zinc Source

Preferably, the zinc source can be selected from commonly available compounds, such as salts of zinc with one or more anions selected from the group consisting of chloride, sulfate, oxide, pyrithione, monophosphate, di- or higher polyphosphate (including but not limited to pyrophosphate, metaphosphate, tripolyphosphate, tetrametaphosphate, and orthophosphate), and anions of mono-, di-, tri-, or poly- organic acids. Of the phosphates, tripolyphosphate is preferred. Of the organic acids, acetate, gluconate, tartrate, fumarate, maleate, malonate, malate, lactate, citrate, EDTA (ethylenediaminetetraacetic acid), citraconate, citramalate, stearate, oleate, laurate, octoate ascorbate, picolinate, and orotate are quite suitable; however, the anions of di-, tri, and poly- organic acids are preferred, with tartrate, citrate, and EDTA being more preferable. The most highly preferred anion in the zinc source is citrate. Mixed salts, i.e. those of zinc with more than one of these anions, or zinc and another acceptable cation with one or more of these anions, are also suitable sources of zinc ion in the present invention. Such mixed salts include without limitation: sodium zinc citrate, magnesium zinc citrate, and zinc stearatelaurate for example.

The Stabilizing Anion

The stabilizing anion is selected from phosphates having more than one —(P=O)—group and organic acids having more than one acid ftmctionality. While it is not impossible to add these materials as free acids, if the resulting pH is too low, the acidity iwill result in destruction of the bicarbonate ion. Hence, these are generally added as soluble salts of the acids, usually as the alkali metal salts, although any acceptable soluble salt may be used. The stabilizing anions suitable in this invention include the non-organic phosphates such as di-, tri-, and higher poly- phosphates; and the anions of di-, tri-, and higher poly- organic acids, such as tartrate, fumarate, maleate, malonate, malate, citraconate, citramalate, lactate, citrate, EDTA (ethylenediaminetetraacetic acid) and the corresponding compounds wherein one or more of the carbonyl groups (—(C=O)—O—) are replaced by —(PO$_4$)—groups. Preferably the stabilizing anion is selected from the group consisting of tripolyphosphate, tartrate, citrate, and EDTA; more preferably, it is citrate. While the cation for the stabilizing anion source can be virtually any suitable cation, it is preferably an alkali metal or magnesium, more preferably sodium or potassium, most preferably, sodium. Since the anions have multiple pKaS, they can exist as mono- or multi- basic forms, any of which will be suitable so long as the pH does not result in destruction of the bicarbonate ion. Where carbonate is present, it can be converted in situ by the more acidic forms of the stabilizing anion to bicarbonate or, if desired, the bicarbonate and/or carbonate ions can be present in sufficient excess so that after reaction with the more acidic forms of the desired stabilizing anion, the concentrations of the zinc ion, bicarbonate and/or carbonate ion, and stabilizing anion are all within the limits set forth in the invention.

While the anion from the zinc source and the stabilizing anion may be different, they are preferably the sarne.

The Bicarbonate and/or Carbonate Source

The bicarbonate and/or carbonate ion source is typically an alkali metal or magnesium bicarbonate and/or carbonate, more preferably sodium and/or potassium salts of bicarbonate and/or carbonate, most preferably, sodium is the cation in the bicarbonate and/or carbonate source. Most preferably the bicarbonate and/or carbonate ion source is a bicarbonate salt.

It is well known that solubilized zinc ion and solubilized bicarbonate and/or carbonate ion will react with each other to form insoluble zinc carbonates. Both of these species are present in the present invention. It has now been found that the presence of a stabilizing anion and the observance of molar equivalent ratios between the zinc ion and the stabilizing anion AND between the stabilizing anion and the bicarbonate and/or carbonate ion permits both the zinc ion and the bicarbonate and/or carbonate ion to coexist in solution in a single phase at levels significantly above those previously known in the absence of the stabilizing anion.

The Molar Equivalent Ratios

The ratio of molar equivalents of stabilizing anion to equivalents of zinc ion must exceed 1.2:1 in the aqueous phase. Preferably it is greater than about 1.4: 1, more preferably greater than about 1.6:1.

The ratio of molar equivalents of bicarbonate and/or carbonate ion to stabilizing anion must be such that the bicarbonate and/or carbonate ion equivalents does not exceed the sum of:

(a) (6)×(the number of equivalents of said di-, tri-, or poly-phosphates); and (b) $\{(3^{(n-1)})/(2^m)\}$×(the number of equivalents of said anions of organic di-, tri-, or poly- acids), where n is the number of carboxyl groups and m is the number of basic nitrogens, if any basic nitrogens are present. (For example, EDTA, which is ethylene diamine teraacetic acid, whether present as the acid or its mono, di, tri, or tetra salt has 4 equivalents of carboxyl groups and 2 equivalents of basic nitrogens per mole of EDTA.) Preferably, portion (a) of the above sum is not greater than about 4×(the number of equivalents of said di-, tri-, or poly- phosphates). Preferably portion (b) of the above sum is not greater than about $\{(2.9^{(n-1)})/(2^m)\}$×(the number of equivalents of said anions of organic di-, tri-, or poly-acids).

If greater amounts of either bicarbonate and/or carbonate are desired and all or a portion of such greater amount is within the solubility of the bicarbonate and/or carbonate respectively, the stabilizing anion content of the aqueous phase solution must be increased sufficiently such that the above relationship between the equivalents of bicarbonate and/or carbonate and the stabilizing anion is maintained in order to maintain a clear solution.

Notwithstanding the above, excess carbonate and bicarbonate may be present in formulations employing the present invention, provided that the excess bicarbonate and excess carbonate are not in solution in the aqueous phase.

Solvent and Vehicle

The main solvent in the vehicle may be totally water or may be an aqueous carrier of diverse compositions adapted for the particular end use. In addition to water, the vehicle may contain (but is not limited to):

auxiliary vehicles such as lower alkyl monohydric alcohols;

humectants (preferably having hydroxy groups) such as mannitol, sorbitol, glycerol, propylene glycol, and propylene glycol;

abrasives such as silica, aluminum oxide, talc;

cavity control agents such as alkali metal fluoride or monofluorophosphate;

tartar control agents such as tetrasodium pyrophosphate;

dental desensitizing agents such as potassium nitrate;

sweeteners such as sodium saccharin, ace-K, aspartame, Sucralose; surfactants, which can be anionic, nonionic, or amphoteric, such as alkali metal alkyl-polyalkoxy sulfate (for example sodium laureth sulfate), alkali metal alkyl sulfate (for example sodium lauryl sulfate), silicone copolyols (for example dimethicone copolyol), betaines (for example cocamidopropyl betaine), ;alkali metal alphaolefin sulfonates, alkylbenzene sulfonates;

foam boosters such as anionic or amphoteric surfactants such as lauramide MEA, alkali metal alkanoyl sarcosinates (for example sodium lauroylsarcosinate), alkali metal cocoylisothionate;

thickeners or viscosity enhancers such as gums (for example carrageenan gum and other galactomannin gums, hydroxypropyl guar gum), silicates such as magnesium aluminum silicate, and cellulosics such as carboxymethylcellulose, hydroxyethylcellulose);

preservatives and antimicrobials such as sodium hydroxymethylglycinate, triclosan, methylparaben;

skin substantive aids;

emulsifiers;

chelating agents such as EDTA;

flavors;

fragrances; and dyes.

Any of the foregoing optional ingredients which one does not desire to incorporate into the aqueous formulation may be included as part of a composition in which the aqueous composition is admixed or taken up, such as in an emulsion (typically a cream or lotion). In such cases, the components which are not in the aqueous phase would be admixed with the non-aqueous phase generally prior to forming the emulsion, cream or lotion. The resulting emulsion can have the aqueous phase as either the internal or external phase of the emulsion, cream, or lotion, as desired for the particular end use.

Other optional ingredients include propellents such as isobutane and propane (for use in aerosol products) and clays or other insoluble absorbent particles in which the aqueous solution of the invention may be adsorbed into or coated onto (for use in animal litter products).

The solutions of the present invention may also be dried (typically by freeze drying to prevent conversion of the bicarbonate to carbonate where that is important to control, but if not, any drying technique in the art would be suitable) to form a powder which is readily dissolvable in aqueous fluids. Such a powder may be utilized in a powder form, compressed into tablets, or filled into capsules (or other suitable containers) for use with aqueous fluids.

While the present invention has been described in terms of a stable clear solution, the invention solutions need not be clear, depending upon the end use. However, upon filtration or centrifuging of the solution which is not clear, the aqueous phase should retain zinc ion in solution along with bicarbonate and/or carbonate ion in solution and one or more stabilizing anions in solution in the ranges specified for the clear solution.

Also within the present invention are solid formulations having appropriate amounts of zinc ion source, stabilizing anion source, and bicarbonate and/or carbonate ion source such that upon being wet with water, a solution within the above described limitations results.

Specific Applications

In each of the following applications, the zinc ion content is referenced to the aqueous phase content of the formulation. The stabilizing anion content remains referenced (as a minimum amount) to the amount of zinc ion. All other component amounts are referenced to the total formulation unless specifically stated otherwise.

Mouthwashes

In the mouthwash field, the zinc source content of the solution is generally present in an amount to yield a zinc ion concentration in the preferred range of about 0.01 to about 1% of the formulation. The solvent may also be plain water or may be water as a major component with minor components of either or both of a lower alkyl monohydric alcohol or a humectant having at least 3 hydroxy groups.

Lower alkyl monohydric alcohols for the invention in the mouthwash field are suitably selected from $C_{1-4}$ alkanols, preferably $C_{2-3}$ alkanols, most preferably ethanol. The alkanols may be either straight chain or branched. When present, the alkanol can be present up to about 30% of the formulation, preferably up to about 25% of the formulation, more preferably about 10 to about 20% of the formulation, still more preferably about 12 to about 15% of the formulation.

The humectant for the invention in the mouthwash field is typically a $C_{3-6}$ compound having at least 3 hydroxy groups. Typical humectants suitable in this invention include, but not limited to, glycerin and sorbitol. When present, the humectant may be present up to about 20% of the formulation, preferably up to about 15% of the formulation, more preferably from about 7 to about 11% of the formulation, most preferably about 9% of the formulation.

In addition, in the mouthwash field, other mouthwash standard ingredients such as surfactants, such as those in the PLURONIC series, especially PLURONIC F-127, antibacterials, such as cetylpyridiniumchloride, flavors, sweeteners, such as sodium saccharine, colors, and thickeners, such as carboxymethylcellulose, may be added as well. When present, the surfactants are used preferably in amounts of up to about 2 weight %; the antibacterials are used in antibacterial effective amounts preferably of up to about 2 weight %; the flavors are used preferably in amounts of up to about 1 weight %, the sweeteners preferably in amounts of up to about 0.6 weight %; the thickeners are used in amounts sufficient to obtain the desired viscosity, preferably in amounts of up to about 0.5 weight %; and the colors are preferably used in amounts of up to about 0.25 weight %; all based on the total formulation. The upper limits on these auxiliary non-essential components may be exceeded when desired without departing from the invention.

Breath Freshener Spray/Liquid Drops

In these applications, zinc source concentration an amount to yield a zinc ion concentration preferably about 0.01 to about 1%, more preferably about 0.05 to about 0.5%. Alkali metal bicarbonate and/or carbonate can range from about 0.5 to about 25 %. Where the alkali metal bicarbonate and/or carbonate exceeds the solubility thereof in the water phase, there need only be sufficient stabilizing anion to be in the proper proportion arelative to the amount of zinc ion and the amount of bicarbonate and/or carbonate which is dissolved in the aqueous phase, although additional stabilizing anion is suitable as well. Humnectants are also present in these formulations in amounts of up to about 20 %. Exemplary humectants include, but are not limited to glycerin, sorbitol, mannitol, etc. Ethyl alcohol can make up as much as 20% of the formulation. Other optional ingredients include, but are not limited to flavors, emulsifiers, sweeteners, and dyes.

Toothpaste/Gel/Polish

In these applications, zinc source concentration is an amount to yield a zinc ion concentration preferably about 0.01 to about 2%, more preferably about 0.05 to about 1.0% of the entire formulation, preferably of the aqueous phase, most preferably of the water content of the formulation. In these formulations, not all of the zinc need be in solution prior to use as there is a substantial dilution of the formulation with water and saliva when in use. In such instances where some of the zinc is not in solution until use, it is most desirable to formulate the product with the more soluble zinc ion sources. This will help insure that the undissolved zinc will be brought into solution more quickly and deliver its intended benefit.

As elsewhere, the stabilizing anion content must be at least 1.2 equivalents per equivalent of zinc ion in solution, although it is much more preferable to have the stabilizing anion present in amounts at least 1.2 equivalents per equivalent of zinc ion if the entire amount of zinc in the formulation were present as dissolved zinc ion.

Alkali metal bicarbonate and/or carbonate can range from about 1 to about 70%. Where the alkali metal bicarbonate and/or carbonate exceeds the solubility thereof in the water phase, there need only be sufficient stabilizing anion to be in the proper proportion relative to the amount of zinc ion and the amount of bicarbonate and/or carbonate which is dissolved in the aqueous phase, although additional stabilizing anion is suitable as well. Humectants are also present in these formulations in amounts of from amounts of from about 5 to about 50%, preferably about 10 to about 40%. Exemplary humectants include, but are not limited to glycerin, sorbitol, mannitol, etc.

These formulations may also contain abrasives in addition to any solid alkali metal bicarbonate and or carbonate which may be present. When present such abrasives can comprise up to about 50% of the formulation. Exemplary, non-limiting abrasives include silicas, aluminum oxide, talc, calcium carbonate, etc. When calcium carbonate is used, it should not be calculated as part of the bicarbonate and/or carbonate ion source as calcium carbonate has very low solubility and does not practically contribute any significant amount of carbonate ion to the solution.

Surfactants may also be present in amounts of from about 0.1 to about 10%, preferably about 0.3 to about 3% of the formulation, and may be selected from anionic, nonionic, and amphoteric surfactants. Typical surfactants include, but are not limited to sodium lauryl sulfate.

Foam boosters, where desired may also be present in amounts of up to about 2% of the formulation. A typical non-limiting example foam booster is sodium lauroyl sarcosinate.

A further optional ingredient in these formulations is a thickener or viscosity enhancer. When present, this component comprises up to about 15% of the formulation. Typical, non-limiting examples include carboxymethylcellulose (or its sodium salt), magnesium aluminum silicate, carrageenan gum, fumed silica, and hydrated silica.

Other typical ingredients in formulation of this type include, but are not limited to a cavity control agent (such as sodium fluoride, monoflurophosphate, etc), a tartar control agent (such as tetrasodium pyrophosphate, etc.), sensitivity reduction agents (such as potassium nitrate, etc.), sweeteners (such as sodium saccharine, ace-K, aspartame, sucralose, etc.), flavors and dyes.

Deodorant Shampoo

For use in this application, the solution should preferably have a zinc source content in an amount to yield a zinc ion concentration in the range of about 0.01% to about 2%, preferably 0.05% to about 0.5%, and alkali metal bicarbonate and/or carbonate (preferably bicarbonate) in an amount of at least 1%. In this application, the clarity of the solution may not be a concern and therefore, the formulation may have excess bicarbonate present not in solution. Clear solutions, where desired, can be obtained up to the maximum solubility of the bicarbonate and/or carbonate and of the stabilizing anion used where the ratio of bicarbonate and/or carbonate to stabilizing anion is maintained in the aqueous solution phase. For sodium bicarbonate maxirnum solubility is about 7% of the available water, while for potassium bicarbonate maximum solubility is about 25% of the available water. Additional bicarbonate, up to about 50% of the formulation, can be tolerated in formulations which do not need to retain clarity.

In these products, surfactants can typically comprise from about 5 to about 30% of the formulation, preferably about 10 to about 20% of the formulation. There is usually no restriction on the surfactants which may be selected in the anionic, nonionic or amphoteric categories. Exemplary surfactants for these formulations include, but are not limited to, sodium laureth sulfate, sodium lauryl sulfate, dimethicone copolyol, and cocamidopropylbetaine.

Foam boosters are frequently included in these products for lather and typically comprise up to 5% of the formulation, when present. Exemplary materials include, but are not limited to lauramide MEA and sodium lauroyl sarcosinate. Thickeners are also an optional item, and when present may comprise up to 10% of the formulation. Typical examples of thickeners in the shampoo area include, but are not limited to carboxymethylcellulose (any form), magnesium aluminum silicate, and natural gums such as carrageenan gum.

Preservatives (for example sodium hydroxymethylglycinate, among others), fragrances, dyes, etc. are also typically in these formulations.

The balance of the formulation is essentially water, but may contain other typical carrier components as well.

Deodorant/Antibacterial Liquid Hand Soap

The zinc, stabilizing anion, and alkali metal bicarbonate and/or carbonate are typically present in these formulations in the same amounts set forth above for the Deodorant Shampoo formulations.

These formulations usually contain from about 5% to about 30% surfactants. The surfactants of choice include, but are not limited to, sodium alphaolefin sulfonates, cocamidopropyl betaines, and alkylbenzene sulfonates.

As with the shampoos, lathering agents or foam boosters are often present and when present comprise up to 5% of the formulation. Examples include, but are not limited to, anionic or amphoteric surfactants. Preferred surfactants include, but are not limited to, lauramnide MEA, sodium lauroylsarcosinate, and sodium cocoylisothionate.

Thickeners or viscosity enhancers may also be present up to about 10% of the formulation. Examples include, but are not limited to, carboxymethylcellulose, hydroxypropylcellulose, hydroxyethylcellulose, hydroxypropyl guar gum, magnesium aluminum silicate, and carrageenan gum.

Other optional ingredients typical to liquid hand soap formulations include, but are not limited to, antimicrobial agents, preservatives, skin substantive aids, chelating agents, fragrances, dyes, etc. A particularly preferred antimicrobial is Triclosan, while a particularly preferred preservative is sodium hydroxymethylglycinate or methylparaben. A preferred chelating agent is EDTA or its salts.

Room Air Deodorizer Spray

In this context, zinc source concentration is an amount to yield a zinc ion concentration about 0.01 to about 1%, preferably 0.05 to about 0.5%. Alkali metal bicarbonate and/or carbonate content may be from about 1 to about 20% of the formulation. Propellants, such as, without limitation, isobutane and propane may comprise up to 30% of the formulation. Pump spray formulations do not need to have any propellant present. In some formulations, excess bicarbonate and/or carbonate may be in the formulation along with an acidulent (which may be slow to dissolve) so as to generate carbon dioxide in situ, the gaseous carbon dioxide to act as the propellant. However, standard propellants such as isobutane, propane, or halogenated hydrocarbons, among others are preferred over in situ carbon dioxide formation. Fragrances are generally present and usually comprise up to about 1% of the formulations.

Fabric/Carpet/Upholstery Deodorizer

Products of this type can generally be formulated in accordance with U.S. Pat. No. 5,593,670, incorporated herein by reference. Both zinc compounds and bicarbonate and/or carbonate compounds are mentioned as possible additional additives there, but under mutually exclusive conditions. In accordance with the present invention, both zinc ion in solution and bicarbonate and/or carbonate ions in solution can be formulated in a single aqueous phase along with the other components of the '670 Patent formulations.

In these applications, the zinc ion source is generally present in an amount to yield a zinc ion concentration of about 0.01 to about 2%, preferably about 0.05 to about 1%, of the aqueous phase. The stabilizing anion is present in an amount that is at least 1.2 equivalent per equivalent of zinc ion. The alkali metal bicarbonate and/or carbonate present in an amount from about 0.1% or higher. For a clear product, the maximum level will be limited based on the amount of water that is available to dissolve the bicarbonate and/or carbonate compounds. This level is typically less than 7% for sodium bicarbonate and 25% for potassium bicarbonate.

To minimize the amount of residue left on the surface after the carrier solution is dried, the preferred level is less than 5%, and the most preferred level is less than 3%. To further minimize the amount of residues on the surface, potassium bicarbonate and/or carbonate is most preferred. This is because residues of potassium salts are less noticeable than those of the corresponding sodium salts.

These formulations also typically include about 0.1% to about 5% solubilized, water-soluble, uncomplexed cyclodextrin, about 0.01% to about 1% low molecular weight polyols. Other optional ingredients include: perfume, water-soluble polymers such as sodium polyacrylates and polyamines, chelating agens such as EDTA, antistatic agents, insetct/moth repelling agents, solubilizing aids, and etc.

The composition can be most advantageously be used in a spray dispenser, pressurized or non-pressurized, or as part of a steam-cleaning solution. It may also be used as a dry powder which is applied and subsequently wet, either due to water present on or in the matterial being treated.

Ostomy Deodorant

In this application, zinc source concentration is an amount to yield a zinc ion concentration about 0.01 to about 2 wt % of the formulation. Alkali metal bicarbonate and/or carbonate is typically present in amounts of from about 1% up to about 25 wt % of the formulation. Stabilizing anion concentration is set at the minimums in the invention to comply with the invention limitations set forth above. In addition, the formulations can have solvents such as alcohols, preferably ethyl alcohol, preservatives, fragrances, and dyes, as may be desired. Typical examples include, but are not limited to, those mentioned in the foregoing applications.

As an alternative, the formulation can be provided as a pre-mixed powder for reconstitution before adding to the ostomy bag. In such cases, the zinc ion source, stabilizing anion and alkali metal bicarbonate and/or carbonate amounts set forth above are the amounts generally used post reconstitution. However, the critical factor is that the powder have the stabilizing anion present in sufficient quantity relative to the zinc and the bicarbonate and/or carbonate such that the stabilizing anion is present in at least 1.2 equivalents per equivalent of zinc ion and at least in an amount so that the bicarbonate and/or carbonate is present in C equivalents
(i.e. no greater than the sum of
(a) (6)×(the number of equivalents of said anions of di-, tri-, or poly-phosphates); and
(b) $\{(3^{(n-1)})/(2^m)\}$×(the number of equivalents of said anions of organic di-, tri-, or poly- acids), where n is the number of carboxyl groups and m is the number of basic nitrogens).

Cat Litter Deodorizer

A solution containing about 0.01 to about 2% zinc ion and the stabilizing anion in at least 1.2 equivalents of anion per equivalent of zinc and preferably sufficiently high such that there is enough stabilizing anion so that a saturated solution of alkali metal bicarbonate and/or carbonate would not be in excess of the amounts permitted by the invention solution above (i.e. no more than C equivalents as defined above) is sprayed onto alkali metal bicarbonate and/or carbonate particles of sufficient size that they do not fully dissolve in the aqueous phase. The coated particles are then combined with appropriate absorbent materials for animal litter such as clays and/or cellulosic materials such as wood shavings, shells, corn husks, etc.

Alternatively, the solution can also contain the desired amount of the bicarbonate and/or carbonate therein and be sprayed onto or absorbed into absorbent litter materials such as clays, absorbent polymers, etc.

Optional ingredients such as fragrances and dyes may also be incorporated into the solution as desired.

Other variations on the above themes for other applications of this invention will be apparent to those of ordinary skill in their respective fields.

Incontinence Pads and Disposable Diapers

Solutions having about 0.01 to about 2 wt % of zinc ion from a suitable zinc ion source and about 1 wt % to about 25 wt % of an alkali metal bicarbonate and/or carbonate are sprayed onto or adsorbed into absorbent materials used in the manufacture of these products. The solutions may contain additional fragrances and preservatives as well as other antibacterials. These auxiliary materials and others need not be part of the solutions being applied and can be present in the final product from other sources if desired.

Alternatively, bicarbonate and/or carbonate beads may have a solution of a zinc source and stabilizing anion sprayed thereon in the amounts specified in the invention (i.e. stabilizing anion present in at least 1.2 equivalents per equivalent of zinc anion and at least an amount C, as defined above).

Toilet Deodorizer/Sanitizer

Products of this nature include solutions which dispense into the toilet tank with each flush as well as solid products which are placed in the toilet tank and dissolve slowly over time. In either case, zinc ion source compounds and alkali metal bicarbonate and/or carbonate compounds can be added to the solution for dispensing or incorporated as dry components in the solid products. The liquid products should adhere to the limitations above for a clear solution so that there will be proper dispensing of usable zinc ion and usable bicarbonate and/or carbonate. The solid product need only be limited to having sufficient amounts so that the water standing in the toilet tank awaiting the next flush adheres to the clear solution limitations above. The other components of such products are well known in the art.

Assembly of the Present Invention Solutions

The various components may be added in essentially any order, but it is highly preferable that the zinc source and the necessary amount of stabilizing anion be brought together in solution prior to contacting the zinc source with the bicarbonate source. This promotes realizing the desired effect more quickly. If the order is reversed and the bicarbonate is contacted with the zinc source in solution before the stabilizing anion is contacted with the zinc source in solution, there is greater risk that insoluble zinc carbonate will result and the resolubilization of the zinc carbonate takes considerable time. It has also been found that the three important components (i.e. the zinc source, the stabilizing anion source, and the alkali metal bicarbonate and/or carbonate) can be brought together as powders and dissolved simultaneously. So long as the relative amounts of the three components in solution are maintained (i.e. the stabilizing anion is present at least in an amount in solution which is at least 1.2 equivalents per equivalent of zinc ion in solution and at least an amount C as defined above), the solution of zinc ion in the presence of bicarbonate and/or carbonate ion will remain sufficiently stable for use in applications which were not previously possible or were not previously possible of commercial utilization.

When sequential dissolution of the materials and clear solutions are desired, generally, the stabilizing anion is dissolved in the water, with mixing until the solution is clear. The zinc source is then added with mixing until the solution is clear. At this point, the primary clear solution of the invention has been achieved. It may be used as is in many of the applications set forth above, modified by adding further ingredients thereto of be incorporated into other base formulations such as creams, gels, or emulsions. Where other ingredients are added to the primary formulation (as opposed to mere incorporation of the primary solution into some other formulation), the remaining ingredients, other than alcohols, surfactants, fragrances and flavors are added with stirring until clear. Then any surfactants, flavors, and fragrances are dissolved in any alcohol which may be present (or if no alcohol any other organic solvent or if none then in additional water) and this last mixture is added to the otherwise complete formulation to arrive at the appropriate solution.

When the primary solution of the invention is to be incorporated into another formulation base, it can be incorporated in the same manner as water would be incorporated into such formulation base, as would be known by those of ordinary skill in the art.

EXAMPLES

Example 1

The following formulations are prepared in the manner set forth below, with the components as set forth in the table below, to yield invention Product A and non-invention Products B and C:

| | Amount (% by weight) | | |
|---|---|---|---|
| Component | Product A | Product B | Product C |
| Zinc Citrate Trihydrate | 0.38 | 0.38 | 0.38 |
| Sodium Citrate Dihydrate | 1.00 | 0.15 | 1.00 |
| Sodium Bicarbonate | 3.00 | 3.00 | 4.75 |
| Water | 73.59 | 74.44 | 71.84 |
| Ethanol | 12.00 | 12.00 | 12.00 |
| Glycerin | 9.00 | 9.00 | 9.00 |
| Pluronic F-127 | 0.45 | 0.45 | 0.45 |
| Cetyl Pyridinium Chloride | 0.10 | 0.10 | 0.10 |
| Flavor | 0.25 | 0.25 | 0.25 |

-continued

| | Amount (% by weight) | | |
|---|---|---|---|
| Component | Product A | Product B | Product C |
| Sodium Saccharine | 0.12 | 0.12 | 0.12 |
| CarboxyMethylCellulose | 0.06 | 0.06 | 0.06 |
| Color | 0.05 | 0.05 | 0.05 |

An aqueous phase mixture is prepared by first adding the sodium citrate to the water with mixing until clear. Next the zinc citrate is added to the aqueous phase with mixing until clear. The carboxymethylcellulose is dispersed in the glycerine and this dispersion is added to the aqueous phase, along with the sodium bicarbonate, sodium saccharin, cetyl pyridinium chloride, and color, with mixing until the solution is clear. An alcoholic phase is prepared separately by adding the Pluronic and the flavor to the ethanol with mixing until the solution is clear. The resulting alcoholic solution is added to the aqueous phase with mixing until the solution is clear to yield the final product.

Example 2

Each of Products A-C are subjected to accelerated stability studies at 122° F. for a period of 4 weeks. The products are examined for the presence of insoluble crystals at different time intervals. Samples are taken after 12 days and after 4 weeks and analyzed for soluble $Zn^{++}$ content. The results appear below.

| Analysis | Storage | Product A | Product B | Product C |
|---|---|---|---|---|
| $Zn^{++}$ Conc. | 12 days | 1370 ppm | 301 ppm | 761 ppm |
| $Zn^{++}$ Conc. | 4 weeks | 1290 ppm | 216 ppm | 384 ppm |
| Amt Insolubles/Crystals | initial | none | significant | none |
| Amt Insolubles/Crystals | 12 days | none | significant | some |
| Amt Insolubles/Crystals | 4 weeks | none | significant | some |

Example 3

Each of the following formulations are prepared using only a source of zinc ion, a source of stabilizing anion, and a bicarbonate source added to 100 grams of water Clarity is examined the same day as preparation.

| | | | | equivalent ratio | | |
|---|---|---|---|---|---|---|
| | gms $ZnCl_2$ | gms NaCitrate[†] | gms $NaHCO_3$ | Anion/ $Zn^{++}$ | $HCO_3^-$/ Anion | solution clarity |
| a | 0.30 | 0 | 3.00 | 0 | infinite | cloudy |
| b | 0.30 | 0.30 | 3.00 | 0.70 | 11.67 | cloudy |
| c | 0.30 | 0.50 | 3.00 | 1.16 | 7.00 | cloudy |
| d | 0.30 | 0.70 | 3.00 | 1.62 | 5.00 | clear |
| e | 0.30 | 0.70 | 6.00 | 1.62 | 10.00 | cloudy |
| f | 0.30 | 1.00 | 3.00 | 2.32 | 3.50 | clear |
| g | 0.30 | 1.00 | 6.00 | 2.32 | 7.00 | clear |
| h | 0.30 | 1.00 | 8.00 | 2.32 | 9.34 | cloudy |

[†]as dihydrate

Example 4

Example 3 is repeated except that differing zinc sources and differing stabilizing anions are used as indicated in the tables.

TABLE I

Citrate as Stabilizing Anion

|   | gms ZnCitrate* | gms NaCitrate† | gms NaHCO$_3$ | equivalent ratio Anion/Zn$^{++}$ | HCO$_3^-$/Anion | solution clarity |
|---|---|---|---|---|---|---|
| a | 0.5 | 0.00 | 4.00 | 1.00 | 9.97 | cloudy |
| b | 0.5 | 0.10 | 4.00 | 1.21 | 8.22 | cloudy |
| c | 0.5 | 0.30 | 4.00 | 1.64 | 6.08 | clear |
| d | 0.5 | 0.30 | 6.00 | 1.64 | 9.12 | cloudy |
| e | 0.5 | 0.50 | 4.00 | 2.07 | 4.82 | clear |
| f | 0.5 | 0.50 | 6.00 | 2.07 | 7.23 | clear |
| g | 0.5 | 0.50 | 7.00 | 2.07 | 8.44 | clear |
| h | 0.5 | 0.50 | 9.00 | 2.07 | 10.85 | cloudy |
| i | 0.5 | 0.70 | 4.00 | 2.50 | 4.00 | clear |

*as trihydrate
†as dihydrate

TABLE II

Citrate/STPP as Stabilizing Anion

|   | gms ZnCitrate* | gms STPP | gms NaHCO$_3$ | solution clarity |
|---|---|---|---|---|
| a | 0.50 | 0.50 | 0 | clear |
| b | 0.50 | 0.50 | 4 | clear |
| c | 0.50 | 0.50 | 6 | clear |
| d | 0.50 | 0.50 | 7 | cloudy |

*as trihydrate

TABLE III

Citrate/EDTA as Stabilizing Anion

|   | gms ZnCitrate* | gms EDTA | gms NaHCO$_3$ | solution clarity |
|---|---|---|---|---|
| a | 0.50 | 0.37 | 0 | clear |
| b | 0.50 | 0.37 | 4 | clear |
| c | 0.50 | 0.37 | 6 | v. cloudy |

*as trihydrate

TABLE IV

Citrate/Tartrate as Stabilizing Anion

|   | gms ZnCitrate* | gms NaTartrate‡ | gms NaHCO$_3$ | solution clarity |
|---|---|---|---|---|
| a | 0.50 | 1.00 | 0 | clear |
| b | 0.50 | 1.00 | 4 | clear |
| c | 0.50 | 1.00 | 6 | v. cloudy |

*as trihydrate
‡as dihydrate

Example 5

Example 4 is repeated using anions which are not within the present invention.

| zinc source | gms amount | anion | gms amount | gms NaHCO$_3$ | solution clarity |
|---|---|---|---|---|---|
| citrate* | 0.5 | sulfate | 2.00 | 4 | v cloudy |
| chloride | 0.3 | chloride | 0.6 | 3 | v. cloudy |
| chloride | 0.3 | sulfate | 1.00 | 3 | v. cloudy |
| gluconate | 1.75 | gluconate | 2.00 | 5 | v. cloudy |

*as trihydrate

Example 6

I claim:

1. A storage clarity-stable aqueous or aqueous/alcoholic solution of zinc ions in the presence of at least one of bicarbonate and carbonate ions comprising:
   (a) a zinc salt of a first anion which salt is selected from the group consisting of
      (i) salts of zinc with one or more of said first anion, including mixed first anion salts thereof, said first anion being selected from the group consisting of
         (1) chloride, sulfate, monophosphate, pyrophosphate, metaphosphate, tripolyphosphate, tettametaphosphate, orthophosphate, and
         (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
      (ii) salts of mixed alkali metal zinc or mixed magnesium zinc with said first anion;
   (b) a salt of a first metal and a second anion; said first metal being selected from the group consisting of alkali metals and magnesium; and said second anion being selected from the group consisting of
      (i) carboxylic acids selected from the group consisting of tartrate, funarate, maleate, malonate, malate, citraconate, citramalate, lactate, citrate, and EDTA, and
      (ii) phosphates selected from the group consisting of pyrophosphate and tripolyphosphate;
   (c) at least one compound selected from the group consisting of alkali metal bicarbonates, alkali metal carbonates, magnesium bicaarbonate, and magnesium carbonate;
   (d) a solvent therefor, said solvent comprising:
      (i) a major proportion of water;
      (ii) optionally a minor amount of a lower alkyl monohydric alcohol; and
      (iii) optionally a minor amount of a humectant having at least 3 hydroxy groups;
   (e) optionally one or more acceptable antibacterial agents;
   (f) optionally one or more acceptable viscosity enhancers;
   (g) optionally one or more sweeteners;
   (h) optionally one of more flavors;
   (i) optionally one or more colors; and
   (j) optionally one or more acceptable fragrances;
   said zinc salt being present in an amount A sufficient to yield a zinc ion concentration of from about 0.01 to about 2 weight %;
   said salt of said second anion present in an amount B, which in combination with any of said second anion present from other components of said solution, is sufficient to provide a total second anion concentration of at least 1.2 equivalents per equivalent of zinc ion;
   said compound being present in an amount of C equivalents, which is no greater than the sum of (a) (6)×(the number of equivalents of said pyrophosphate and tripolyphosphate); and (b) $\{(3^{(n-1)})/(2^m)\}$×(the number of equivalents of said second anions which are carboxylic acids), where n is the number of carboxyl groups and m is the number of basic nitrogens;

whereby the interaction of solubilized zinc ions and solubilized bicarbonate and carbonate ions to form insoluble zinc carbonate(s) is substantially reduced relative to that which would occur in the same formulation in the absence of said second anion in the amounts set forth above.

2. The solution of claim 1 wherein said first anion is selected from the group consisting of chloride, sulfate, gluconate, tartrate, fumarate, maleate, malonate, lactate, citrate, EDTA, citraconate, citramalate, stearate, oleate, laurate, and octoate.

3. The solution of claim 2 wherein said first anion is citrate.

4. The solution of claim 2 wherein said zinc salt of said first anion is zinc citrate trihydrate.

5. The solution of claim 1 wherein said second anion is selected from the group of consisting of tripolyphosphate, pyrophosphate, fumarate, tartrate, maleate, malonate, citraconate, citramalate, lactate, citrate, and EDTA ion.

6. The solution of claim 5 wherein said second anion is citrate.

7. The solution of claim 5 wherein said salt of said first metal and said second anion is sodium citrate.

8. The solution of claim 7 wherein said sodium citrate is sodium citrate dihydrate.

9. The solution of claim 1 wherein said first anion and said second anion are the same.

10. The solution of claim 9 wherein said alkali metal bicarbonate is sodium bicarbonate and said alkali metal carbonate is sodium carbonate.

11. The solution of claim 1 wherein said first metal and the cation said compound are the same.

12. A storage clarity-stable aqueous or aqueous/alcoholic solution of zinc ions in the presence of at least one of bicarbonate ions and carbonate ions which results from providing, in a single solution:

(a) a zinc ion source which is a zinc salt of a first anion which salt is selected from the group consisting of
  (i) salts of zinc with one or more of said first anion, including mixed first anion salts thereof, said first anion being selected from the group consisting of
    (1) chloride, sulfate, monophosphate, pyrophosphate, metaphosphate, tripolyphosphate, tetrametaphosphate, orthophosphate, and
    (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
  (ii) salts of mixed alkali metal/zinc or mixed magnesium/zinc with said first anion;

(b) a source of a stabilizing anion which stabilizes solutions of zinc ions in the presence of bicarbonate and/or carbonate ions, which source is a salt of a first metal and a second anion, said first metal being selected from the group consisting of alkali metals and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;

(c) a bicarbonate and/or carbonate ion source selected from the group consisting of alkali metal bicarbonate, alkali metal carbonate, magnesium bicarbonate, and magnesium carbonate;

(d) a solvent therefor, said solvent comprising:
  (i) a major proportion of water;
  (ii) optionally a minor amount of a lower alkyl monohydric alcohol; and
  (iii) optionally a minor amount of a humectant having at least 3 hydroxy groups;

(e) optionally one or more acceptable antibacterial agents;

(f) optionally one or more acceptable viscosity enhancers;

(g) optionally one or more sweeteners;

(h) optionally one of more flavors;

(i) optionally one or more colors; and (j) optionally one or more fragrances;

said zinc salt being present in an amount A sufficient to yield a zinc ion concentration of from about 0.01 to about 2 weight %;

said salt of said second anion present in an amount B, which in combination with any of said second anion present from other components of said solution, is sufficient to provide a total second anion concentration of at least 1.2 equivalents per equivalent of zinc ion;

said bicarbonate and carbonate ion source being present in a combined amount of C equivalents, which is no greater than the sum of (a) (6)×(the number of equivalents of said pyrophosphate and tripolyphosphate); and (b) $\{(3^{(n-1)})/(2^m)\}$×(the number of equivalents of said second anions which are carboxylic acids), where n is the number of carboxyl groups and m is the number of basic nitrogens whereby the interaction of solubilized zinc ions with solubilized bicarbonate and/or carbonate ions to form insoluble zinc carbonate(s) is substantially reduced relative to that which would occur in the same formulation in the absence of said second anion in the amounts set forth above.

13. A method of maintaining zinc ions and at least one of bicarbonate ions and carbonate ions in a single phase aqueous or aqueous/alcoholic solution of claim 1 comprising contacting a stabilizing amount of a stabilizing anion with zinc ions and at least one of said bicarbonate ions and carbonate ions wherein said stabilizing anion is selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate. said zinc ion being present in an amount of from about 0.01 to about 2 weight %; said stabilizing anion being present in an amount B, which in combination with any of said stabilizing anion present from other components of said solution, is sufficient to provide a total stabilizing anion concentration of at least 1.2 equivalents per equivalent of zinc ion;

said bicarbonate and carbonate ion source being present in a combined amount of C equivalents, which is no greater than the sum of (a) (6)×(the number of equivalents of said pyrophosphate and tripolyphosphate); and (b) $\{(3^{(n-1)})/(2^m)\}$×(the number of equivalents of said second anions which are carboxylic acids), where n is the number of carboxyl groups and m is the number of basic nitrogens whereby the interaction of solubilized zinc ions with solubilized bicarbonate and/or carbonate ions to form insoluble zinc carbonate(s) is substantially reduced relative to that which would occur in the same formulation in the absence of said second anion in the amounts set forth above.

14. A storage clarity-stable aqueous or aqueous/alcoholic solution of claim 1 of zinc ions in the presence of at least one of bicarbonate ions and carbonate ions which results from providing, in a single solution, a combination consisting essentially of:
   (a) a zinc ion source which is a zinc salt of a first anion which salt is selected from the group consisting of
      (i) salts of zinc with one or more of said first anion, including mixed first anion salts thereof, said first anion being selected from the group consisting of
         (1) chloride, sulfate, monophosphate, pyrophosphate, metaphosphate, tripolyphosphate, tetrametaphosphate, orthophosphate, and
         (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
      (ii) salts of mixed alkali metal/zinc or mixed magnesium/zinc with said first anion;
   (b) a source of a stabilizing anion which stabilizes solutions of zinc ions in the presence of bicarbonate ions and/or carbonate ions, which source is a salt of a first metal and a second anion, said first metal being selected from the group consisting of alkali metal and magnesium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;
   (c) a bicarbonate ion source selected from the group consisting alkali metal bicarbonate, alkali metal carbonate, magnesium bicarbonate, and magnesium carbonate;
   (d) a solvent therefor, said solvent comprising:
      (i) a major proportion of water;
      (ii) optionally a minor amount of a lower alkyl monohydric alcohol; and
      (iii) optionally a minor amount of a humectant having at least 3 hydroxy groups;
   (e) optionally one or more acceptable antibacterial agents;
   (f) optionally one or more acceptable viscosity enhancers;
   (g) optionally one or more sweeteners;
   (h) optionally one of more flavors;
   (i) optionally one or more colors; and
   optionally one or more fragrances;
   said zinc salt being present in an amount A sufficient to yield a zinc ion concentration of from about 0.01 to about 2 weight %;
   said salt of said second anion present in an amount B, which in combination with any of said second anion present from other components of said solution, is sufficient to provide a total second anion concentration of at least 1.2 equivalents per equivalent of zinc ion;
   said bicarbonate and carbonate source being present in a combined amount of C equivalents, which is no greater than the sum of
   (a) (6)×(the number of equivalents of said pyrophosphate and tripolyphosphate); and
   (b) $\{(3^{(n-1)})/(2^m)\}\times$(the number of equivalents of said second anions which are carboxylic acids), where n is the number of carboxyl groups and m is the number of basic nitrogens whereby said storage clarity-stable aqueous or aqueous/alcoholic single phase solution remains clear and free of cloudiness or insoluble crystals or basic salts of zinc and carbonate(s) during storage, said zinc ions and said bicarbonate and/or carbonate ions being provided in amounts which are effective for the prevention and counteraction of malodors.

15. A storage clarity-stable aqueous or aqueous/alcoholic single phase solution of zinc ions in the presence of at least one of bicarbonate ions and carbonate ions comprising:
   (a) a zinc salt of a first anion which salt is selected from the group consisting of
      (i) salts of zinc with one or more of said first anion, including mixed first anion salts thereof, said first anion being selected from the group consisting of
         (1) chloride, sulfate, monophosphate, pyrophosphate, metaphosphate, tripolyphosphate, tetrametaphosphate, orthophosphate, and
         (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
      (ii) salts of mixed alkali metal zinc or mixed magnesium zinc with said first anion;
   (b) a salt of a first metal and a second anion, said first metal being selected from the group consisting of sodium and potassium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;
   (c) at least one alkali metal bicarbonate and/or alkali metal carbonate;
   (d) a solvent therefor, said solvent comprising:
      (i) a major proportion of water;
      (ii) optionally a minor amount of a lower alkyl monohydric alcohol; and
      (iii) optionally a minor amount of a humectant having at least 3 hydroxy groups;
   (e) optionally one or more acceptable antibacterial agents;
   (f) optionally one or more acceptable viscosity enhancers;
   (g) optionally one or more sweeteners;
   (h) optionally one of more flavors;
   (i) optionally one or more colors; and
   (j) optionally one or more fragrances;
   said zinc salt being present in an amount A sufficient to yield a zinc ion concentration of from about 0.01 to about 2 weight %;
   said salt of said second anion present in an amount B, which in combination with any of said second anion present from other components of said solution, is sufficient to provide a total second anion concentration of at least 1.2 equivalents per equivalent of zinc ion;
   said at least one alkali metal bicarbonate and/or carbonate, together being present in an amount of C equivalents, which is no greater than the sum of
   (a) (6)×(the number of equivalents of said pyrophosphate and tripolyphosphate); and (b) $\{(3^{n-1})/(2^m)\}\times$(the number of equivalents of said second anions which are carboxylic acids), where n is the number of carboxyl groups and m is the number of basic nitrogens;

whereby said storage clarity-stable aqueous or aqueous/alcoholic single phase solution remains clear and free of cloudiness or insoluble crystals or basic salts of zinc and carbonate(s) during storage, said zinc ions and said bicarbonate ions and/or carbonate ions being provided in amounts which are effective for the prevention and counteraction of malodors.

16. A method of preparing a storage clarity-stable aqueous or aqueous/alcoholic solution of claim 1 consisting essentially of:

(a) a zinc ion source which is a zinc salt of a first anion which salt is selected from the group consisting of
  (i) salts of zinc with one or more of said first anion, including mixed first anion salts thereof, said first anion being selected from the group consisting of
    (1) chloride, sulfate, monophosphate, pyrophosphate, metaphosphate, tripolyphosphate, tetrametaphosphate, orthophosphate, and
    (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
  (ii) salts of mixed alkali metal/zinc or mixed magnesium/zinc with said first anion;

(b) a source of a stabilizing anion which stabilizes solutions of zinc ions in the presence bicarbonate ions, which source is a salt of a first metal and a second anion, said first metal being selected from the group consisting of sodium and potassium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;

(c) a bicarbonate ion source selected from the group consisting of sodium bicarbonate and potassium bicarbonate;

(d) a solvent therefor, said solvent comprising:
  (i) a major proportion of water;
  (ii) optionally a minor amount of a lower alkyl monohydric alcohol; and
  (iii) optionally a minor amount of a humectant having at least 3 hydroxy groups;

(e) optionally one or more acceptable antibacterial agents;

(f) optionally one or more acceptable viscosity enhancers;

(g) optionally one or more sweeteners;

(h) optionally one of more flavors;

(i) optionally one or more colors; and (j) optionally one or more fragrances;

said zinc salt being present in an amount A sufficient to yield a zinc ion concentration of from about 0.01 to about 2 weight %;

said salt of said second anion present in an amount B, which in combination with any of said second anion present from other components of said solution, is sufficient to provide a total second anion concentration of at least 1.2 equivalents per equivalent of zinc ion;

said bicarbonate source being present in an amount of C equivalents, which is no greater than the sum of (a) (6)×(the number of equivalents of said pyrophosphate and tripolyphosphate); and (b) $\{(3^{(n-1)})/(2m)\}\times$(the number of equivalents of said second anions which are carboxylic acids), where n is the number of carboxyl groups and m is the number of basic nitrogens whereby said storage clarity-stable aqueous or aqueous/alcoholic single phase solution remains clear and free of cloudiness or insoluble crystals or basic salts of zinc and carbonate(s) during storage, said zinc ions and said bicarbonate ions being provided in amounts which are effective for the prevention and counteraction of malodors;

said method comprising contacting said stabilizing amount of said stabilizing anion with said zinc ions and said bicarbonate ions.

17. The method of claim 16 wherein said stabilizing anions are contacted with said zinc ions prior to the addition of said bicarbonate ions.

18. A method of using the solution of claim 1 comprising incorporating said solution of claim 1 into a product selected from a mouthwash, a breath freshener spray, a breath freshener drop formulation, a toothpaste, a toothgel, a tooth polish, a deodorant shampoo, a deodorant hand soap, a room air deodorizer spray, an ostomy deodorant, an animal litter deodorizer, an animal litter, incontinence pads, disposable diapers, fabric deodorizer, carpet deodorizer, upholstery deodorizer, and toilet deodoraizers and santizers.

19. The solution of claim 1 wherein said solution further optionally contains at least one of (k) an abrasive;
(l) a cavity control agent;
(m) a tartar control agent;
(n) a dental desensitizer;
(o) a surfactant;
(p) a foam booster;
(q) a preservative;
(r) a skin substantive aid;
(s) an emulsifier;
(t) a chelating agent; and
(u) a propellant.

20. The solution of claim 1 wherein said zinc salt is zinc citrate trihydrate, said salt of a first metal and a second anion is sodium citrate, and said compound is sodium bicarbonate.

* * * * *